US00PP18011P2

(12) United States Plant Patent
Jepsen

(10) Patent No.: US PP18,011 P2
(45) Date of Patent: Sep. 11, 2007

(54) ***KALANCHOE* PLANT NAMED 'YAZMIN'**

(50) Latin Name: *Kalanchoe blossfeldiana*
Varietal Denomination: Yazmin

(75) Inventor: Knud Jepsen, Hinnerup (DK)

(73) Assignee: Knud Jepsen A/S, Hinnerup (DK)

( * ) Notice: Subject to any disclaimer, the term of this patent is extended or adjusted under 35 U.S.C. 154(b) by 0 days.

(21) Appl. No.: 11/358,831

(22) Filed: Feb. 17, 2006

(51) Int. Cl.
*A01H 5/00* (2006.01)

(52) U.S. Cl. ..... Plt./336

(58) Field of Classification Search ..... Plt./335, Plt./336

See application file for complete search history.

*Primary Examiner*—Anne Marie Grunberg
*Assistant Examiner*—S. B. McCormick-Ewoldt
(74) *Attorney, Agent, or Firm*—C. A. Whealy

(57) ABSTRACT

A new and distinct cultivar of *Kalanchoe* plant named 'Yazmin', characterized by its upright and uniform plant habit; large white-colored double flowers with about 45 petals per flower; and excellent postproduction longevity.

1 Drawing Sheet

Botanical designation: *Kalanchoe blossfeldiana.*
Cultivar denomination: 'Yazmin'.

BACKGROUND OF THE INVENTION

The present invention relates to a new and distinct cultivar of *Kalanchoe* plant, botanically known as *Kalanchoe blossfeldiana,* and hereinafter referred to by the name 'Yazmin'.

The new *Kalanchoe* is a product of a planned breeding program conducted by the Inventor in Hinnerup, Denmark. The objective of the breeding program was to create new freely-flowering *Kalanchoe* cultivars with large flowers, numerous petals per flower, attractive flower coloration and excellent postproduction longevity.

The new *Kalanchoe* originated from a cross-pollination made on Nov. 24, 2004 in Hinnerup, Denmark, of the *Kalanchoe blossfeldiana* cultivar KJ 2003 0818, disclosed in U.S. Plant patent application Ser. No. 11/080,401, as the female, or seed, parent with the *Kalanchoe blossfeldiana* cultivar Simone 2000, disclosed in U.S. Plant Pat. No. 12,319, as the male, or pollen, parent. The new *Kalanchoe* was discovered and selected by the Inventor as a single flowering plant within the progeny of the stated cross-pollination grown in a controlled environment in Hinnerup, Denmark in June, 2005.

Asexual reproduction of the new *Kalanchoe* by terminal cuttings at Hinnerup, Denmark since July, 2005, has shown that the unique features of this new *Kalanchoe* are stable and reproduced true to type in successive generations.

BRIEF SUMMARY OF THE INVENTION

The cultivar Yazmin has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yazmin'. These characteristics in combination distinguish 'Yazmin' as a new and distinct cultivar:

1. Upright and uniform plant habit.
2. Large white-colored double flowers with about 45 petals per flower.
3. Excellent postproduction longevity.

Plants of the new *Kalanchoe* can be compared to plants of the female parent, the cultivar KJ 2003 0818. Plants of the new *Kalanchoe* differ from plants of the cultivar KJ 2003 0818 in leaf and flower color as plants of the cultivar KJ 2003 0818 have darker green-colored leaves and light pink-colored flowers.

Plants of the new *Kalanchoe* can be compared to plants of the male parent, the cultivar Simone 2000. Plants of the new *Kalanchoe* differ from plants of the cultivar Simone 2000 in flower shape and size and shape as plants of the cultivar Simone 2000 have single flowers that are smaller in size than flowers of plants of the new *Kalanchoe.*

Plants of the new *Kalanchoe* can also be compared to plants of the *Kalanchoe* cultivar KJ 2003 0852, disclosed in U.S. Plant Pat. No. 17,528. In side-by-side comparisons, plants of the new *Kalanchoe* differ from plants of the cultivar KJ 2003 0852 in the following characteristics:

1. Plants of the new *Kalanchoe* were not as vigorous as plants of the cultivar KJ 2003 0852.
2. Plants of the new *Kalanchoe* had ovate-shaped leaves whereas plants of the cultivar KJ 2003 0852 had elliptic-shaped leaves.
3. Plants of the new *Kalanchoe* had larger inflorescences with more flowers per inflorescence than plants of the cultivar KJ 2003 0852.
4. Plants of the new *Kalanchoe* had larger flowers with more petals per flower than plants of the cultivar KJ 2003 0852.
5. Plants of the new *Kalanchoe* flowered about six days earlier than plants of the cultivar KJ 2003 0852.

BRIEF DESCRIPTION OF THE PHOTOGRAPHS

The accompanying colored photographs illustrate the overall appearance of the new *Kalanchoe,* showing the colors as true as it is reasonably possible to obtain in colored reproductions of this type. Colors in the photographs may differ slightly from the color values cited in the detailed botanical description which accurately describe the colors of the new *Kalanchoe*. The photographs were taken under diffuse natural light conditions on a sunny day at approximately noon in Hinnerup, Denmark.

The photograph at the top of the sheet comprises a side perspective view of a typical flowering potted plant of 'Yazmin'.

The photograph at the bottom of the sheet comprises a top perspective view of a typical flowering plant of 'Yazmin'.

DETAILED BOTANICAL DESCRIPTION

In the following description, color references are made to The Royal Horticultural Society Colour Chart, 2001 Edition, except where general terms of ordinary dictionary significance are used. Plants used in the photographs and for the following description were grown in Hinnerup, Denmark, under commercial practice in a glass-covered greenhouse for about 16 weeks with day temperatures about 19° C., night temperatures about 21° C. and light levels ranging from 10 to 50 kilolux. Plants used in the description and photographs were not pinched. Unless otherwise specified, the leaf description represents leaves from a vegetative plant.

Botanical classification: *Kalanchoe blossfeldiana* cultivar Yazmin.

Parentage:

*Female, or seed, parent.*—*Kalanchoe blossfeldiana* cultivar KJ 2003 0818, disclosed in U.S. Plant patent application Ser. No. 11/080,401.

*Male, or pollen, parent.*—*Kalanchoe blossfeldiana* cultivar Simone 2000, disclosed in U.S. Plant Pat. No. 12,319.

Propagation:

*Type cutting.*—Terminal cuttings.

*Time to initiate roots, summer.*—About two weeks at 19° C. to 21° C.

*Time to initiate roots, winter.*—About three weeks at 19° C. to 21° C.

*Time to produce a rooted young plant, summer.*—About three weeks at 19° C. to 21° C.

*Time to produce a rooted young plant, winter.*—About 24 days at 19° C. to 21° C.

*Root description.*—Fine, fibrous; white in color.

*Rooting habit.*—Freely branching.

Plant description:

*Form.*—Upright and uniform plant habit with numerous compound cymes; freely flowering. Moderately vigorous growth habit.

*Branching habit.*—Freely branching, about five lateral branches develop on non-pinched plants. Pinching (removal of terminal apex) is not required but will enhance lateral branch development.

*Plant height at flowering.*—About 25 cm.

*Plant diameter at flowering.*—About 20 cm.

*Lateral branch description.*—Length: About 13 cm. Diameter: About 4 mm. Internode length: About 1 cm. Texture: Smooth, glabrous. Strength: Strong. Color 146B.

*Foliage description.*—Arrangement: Opposite, simple. Size: Leaf size is reduced after floral induction. Vegetative plants: Length: About 9 cm. Width: About 4 cm to 7 cm. Reproductive plants: Length: About 5 cm to 9 cm. Width: About 4 cm to 7 cm. Shape: Ovate. Apex: Rounded. Base: Obtuse. Margin: Crenate. Aspect: Concave and twisting. Texture, upper and lower surfaces: Smooth, glabrous; leathery; succulent. Color: Developing and fully expanded foliage, upper surface: 146A; venation, close to 146A. Developing and fully expanded foliage, lower surface: 146B; venation, close to 146B. Petiole: Length: About 1.5 cm. Diameter: About 7 mm. Texture: Smooth, glabrous. Color, upper surface: 146B. Color, lower surface: 146C.

Flower description:

*Flower type and habit.*—Double flowers arranged in compound dichasial cymes that arise from leaf axils. Upright flowering stems. Freely flowering, about one to three inflorescences per lateral branch each inflorescence with about 10 to 20 flowers. Flowers persistent.

*Natural flowering season.*—Plants planted in an outdoor nursery will flower from April to October in The Netherlands. Flower initiation and development can be induced under short day/long night conditions in the greenhouse year-round.

*Time to flower.*—From the start of the short day/long night conditions, plants flower about 72 days later. Time to flower is primarily dependent upon temperature and light intensity.

*Flower opening.*—First flower open is the terminal flower at the main axis and is followed by the opening of the terminal flowers of the side branches of the inflorescence. About 1.5 weeks after the first flower has opened, 25% of the remaining flowers are open.

*Post-production longevity.*—Plants of the new *Kalanchoe* maintain good leaf and flower substance for about six weeks under interior environmental conditions.

*Inflorescence height.*—About 13 cm.

*Inflorescence diameter.*—About 7 cm.

*Flower diameter.*—About 2.7 cm.

*Flower depth (height).*—About 1.3 cm.

*Flower buds.*—Shape: Oblong. Length: About 1.5 cm. Width, mid-section: About 9 mm. Color: 144D.

*Petals.*—Quantity: Typically about 35 to 45 per flower. Length: About 1.2 cm. Diameter: About 8 mm. Shape: Ovate. Apex: Cuspidate. Base: Fused. Margin: Entire. Texture, upper and lower surfaces: Glabrous, smooth. Color: When opening, upper surface: Close to 155D. When opening, lower surface: Close to 155C. Fully opened, upper and lower surfaces: Close to 155D.

*Sepals.*—Quantity: About four per flower. Length: About 1 cm. Diameter: About 2 mm. Shape: Lanceolate. Apex: Acute. Base: Truncate. Margin: Entire. Texture, upper and lower surfaces: Glabrous, smooth. Color: When opening and fully opened, upper surface: 146B. When opening and fully opened, lower surface: 146C.

*Peduncles.*—Length: About 4 mm to 6 mm. Diameter: About 1.2 mm to 1.5 mm. Strength: Strong. Angle: Erect to about 90° from vertical. Texture: Smooth, glabrous. Color: 146B.

*Reproductive organs.*—Stamens: Anther size: About 1 mm by 1 mm. Anther shape: Elliptic. Anther color: 19A. Pollen color: 20A. Pistils: Number of pistils per flower: About four. Pistil length: About 8 mm. Style length: About 2 mm. Style color: 145A. Stigma color: 145A. Stigma shape: Round. Ovary color: 144A.

*Seeds.*—Number of seeds per ovary: About 50 to 60. Size: Less than 1 mm by less than 1 mm. Color, immature: 145C. Color, mature: 177A.

Disease/pest resistance: Resistance to known pathogens and pests common to *Kalanchoe* has not been observed on plants of the new *Kalanchoe* grown under commercial greenhouse conditions.

Temperature tolerance: Plants of the new *Kalanchoe* have been observed to tolerate temperatures from about 5° C. to about 30° C.

It claimed:

1. A new and distinct cultivar of *Kalanchoe* plant named 'Yazmin', as illustrated and described.

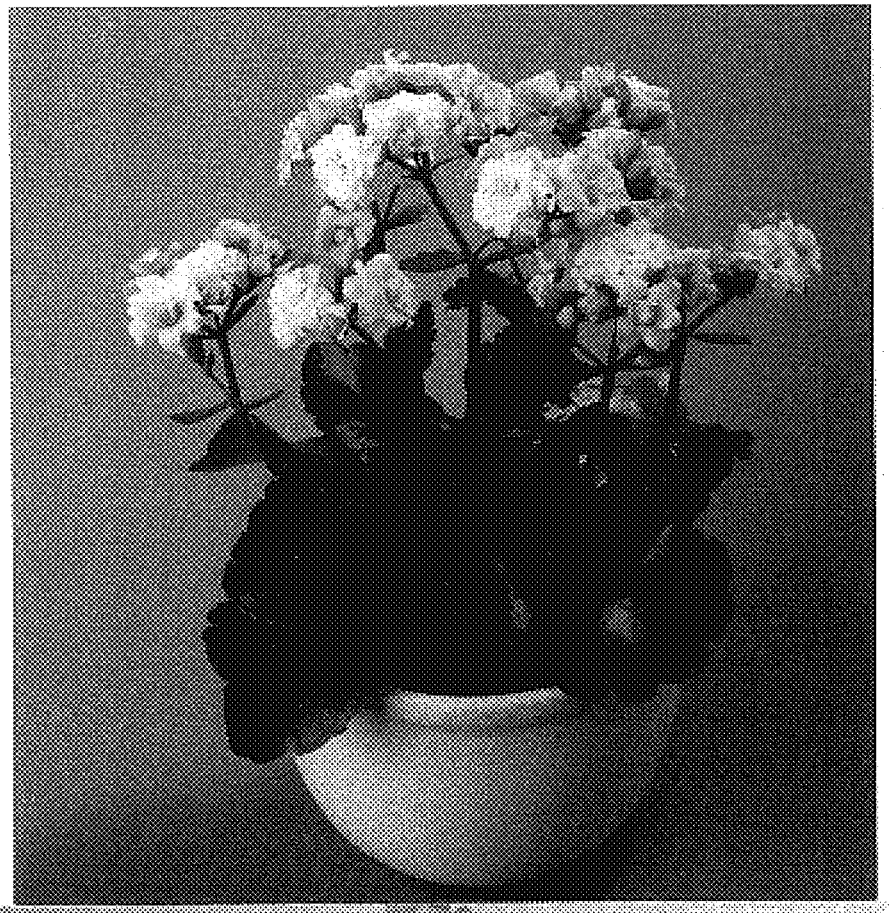
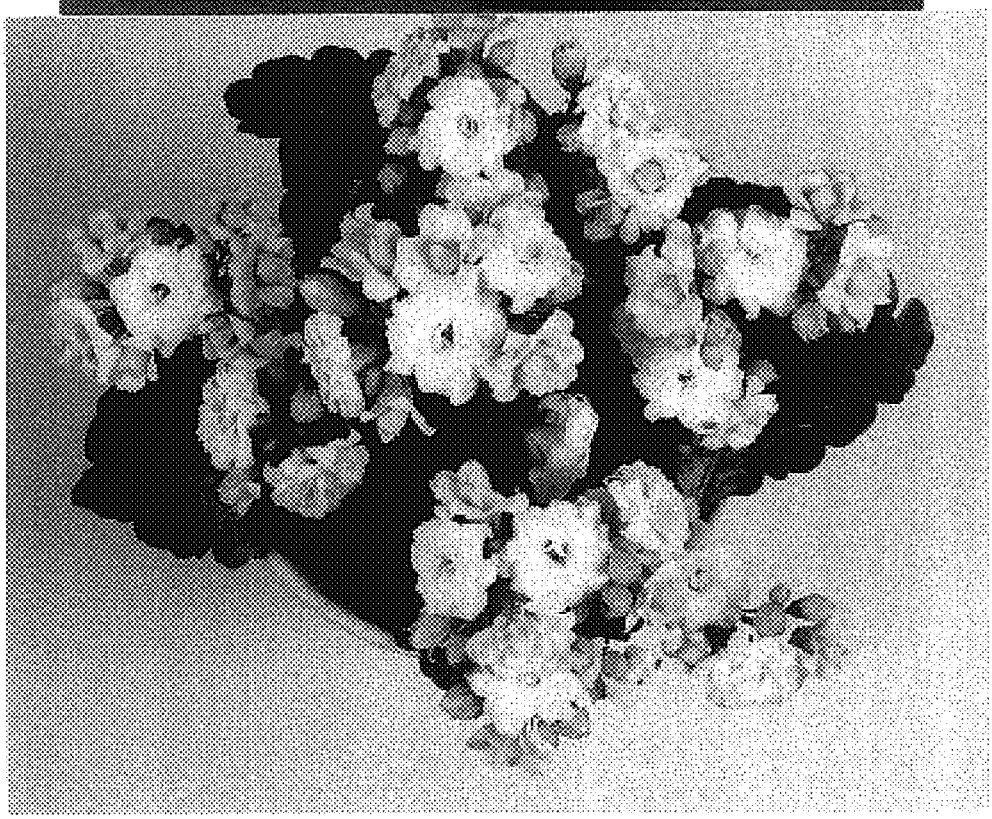

* * * * *